United States Patent [19]
Cardo et al.

[11] Patent Number: 5,000,747
[45] Date of Patent: Mar. 19, 1991

[54] OSTOMY APPLIANCE CLOSURE DEVICE

[76] Inventors: Alexander J. Cardo; Grace Cardo, both of 3402 Crape Myrtle Dr., Hernando Beach Spring Hill, Fla. 34607

[21] Appl. No.: 519,786
[22] Filed: May 7, 1990
[51] Int. Cl.⁵ .............................................. A61M 1/00
[52] U.S. Cl. ................................ 604/317; 24/30.5 R; 24/30.5 S
[58] Field of Search ........... 24/30.5 R, 30.5 P, 30.5 S, 24/129 D, DIG. 28, 545, 67.9, 30.5 L, 30.5 W; 604/317, 342, 340

[56] References Cited
U.S. PATENT DOCUMENTS
3,100,324  8/1963  Tutino et al. ........................ 24/346

Primary Examiner—Randall L. Green
Assistant Examiner—Trinh Nguyen
Attorney, Agent, or Firm—Leon Gilden

[57] ABSTRACT

An ostomy bag closure organization includes a polymeric block formed with an elongate slit positioned medially of the block parallel to spaced parallel sides of the block with spaced arcuate recesses positioned within a forward and end surface of the block for receiving first and second resilient bands in a parallel relationship in a first position and in a crossed relationship in a second position to bias the bifurcated block in a secure position relative to an associated bag inserted and wound about the block. The resilient bands are secured within respective slits directed interiorly of the block at intersections of the side walls and end wall of the block.

5 Claims, 2 Drawing Sheets

OSTOMY APPLIANCE CLOSURE DEVICE

BACKGROUND OF THE INVENTION

1. Field of the Invention

The field of invention relates to bag closure organizations, and more particularly pertains to a new and improved ostomy pouch closure device wherein the same enables selective closure of associated ostomy pouches.

2. Description of the Prior Art

The use of ostomy bags subsequent to particular surgical procedures is known in the prior art. Disposal of feces and temporary closure of the bag is desirable by individuals requiring their use.

Examples of the prior art include U.S. Pat. No. 3,022,786 to Nalon setting forth a colostomy belt provided with a sack container mounted to a belt portion by use of an elongate elastomeric ring.

U.S. Pat. No. 3,964,485 to Neumeier includes an abdominal wall contacting gasket element with an apertured gasket back wall portion which is relatively convex and flexible for attachment of a storage pouch to the gasket member.

U.S. Pat. No. 3,736,934 to Hennessey sets forth a colostomy type securement organization wherein a gasket member is adhered to the skin portion with a spout opening oriented for securement of a bag member thereto.

U.S. Pat. No. 3,869,762 to Barrett sets forth a colostomy bag securement arrangement wherein a rigid base gasket and expandable retainer ring secures the attached bag or pouch to the base gasket for use.

U.S. Pat. No. 2,869,548 to Mason sets forth a multielement colostomy pouch securement arrangement including an annular spring member to secure the pouch to an associated grooved gasket portion.

As such, it may be appreciated that there is a continuing need for a new and improved ostomy pouch closure device which addresses both the problems of comfort in use and convenience in effectiveness in operation, and in this respect, the present invention substantially fulfills this need in contradistinction to prior art devices as exemplified above.

SUMMARY OF THE INVENTION

In view of the foregoing disadvantages inherent in the known types of ostomy bag devices now present in the prior art, the present invention provides an ostomy pouch closure device wherein the same utilizes a slot or gap to receive an ostomy pouch therethrough to enable biasing of opposed surfaces defining the slot or gap to effect closure of the associated bag. As such, the general purpose of the present invention, which will be described subsequently in greater detail, is to provide a new and improved ostomy pouch closure device which has all the advantages of the prior art ostomy bag devices and none of the disadvantages.

To attain this, the ostomy bag closure device includes a bifurcated block formed of a polymeric memory retentent material with the block defined by a medial slot spaced parallel to opposed elongate sides of the block. Arcuate grooves are positioned in an aligned pair at a forward end of the block secured within respective slot at rear corner portions of the block to contain and secure the ostomy pouch within a medical groove defined by the block.

My invention resides not in any one of these features per se, but rather in the particular combination of all of them herein disclosed and claimed and it is distinguished from the prior art in this particular combination of all of its structures for the functions specified.

There has been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved ostomy bag closure device which has all the advantages of the prior art ostomy bag devices and none of the disadvantages.

It is another object of the present invention to provide a new and improved ostomy bag closure device which may be easily and efficiently manufactured and marketed.

It is a further object of the present invention to provide a new and improved ostomy bag closure device which is of a durable and reliable construction.

An even further object of the present invention is to provide a new and improved ostomy bag closure device which is susceptible of a low cost of manufacture with regard to both materials and labor, and which accordingly is then susceptible of low prices of sale to the consuming public, thereby making such ostomy bag closure devices economically available to the buying public.

Still yet another object of the present invention is to provide a new and improved ostomy bag closure device which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
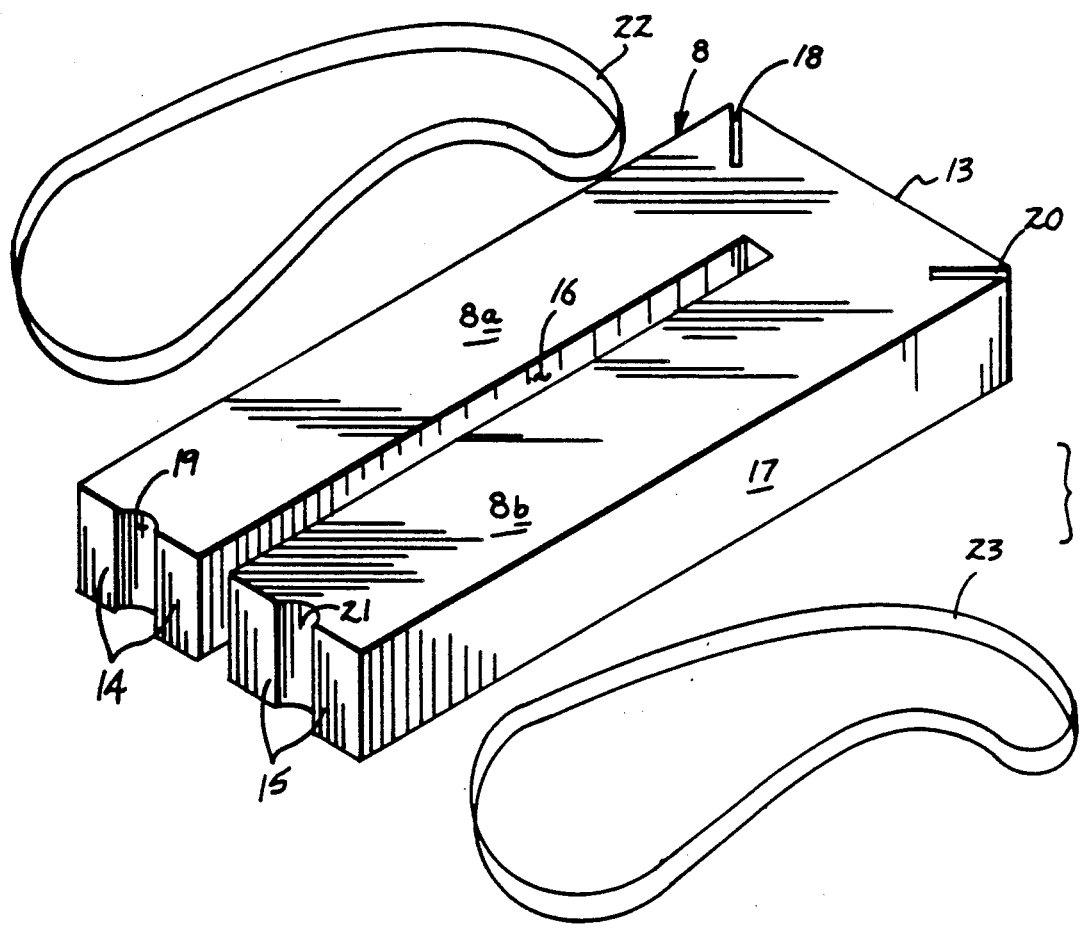
FIG. 1 is an isometric illustration of the instant invention.
Figure 2:
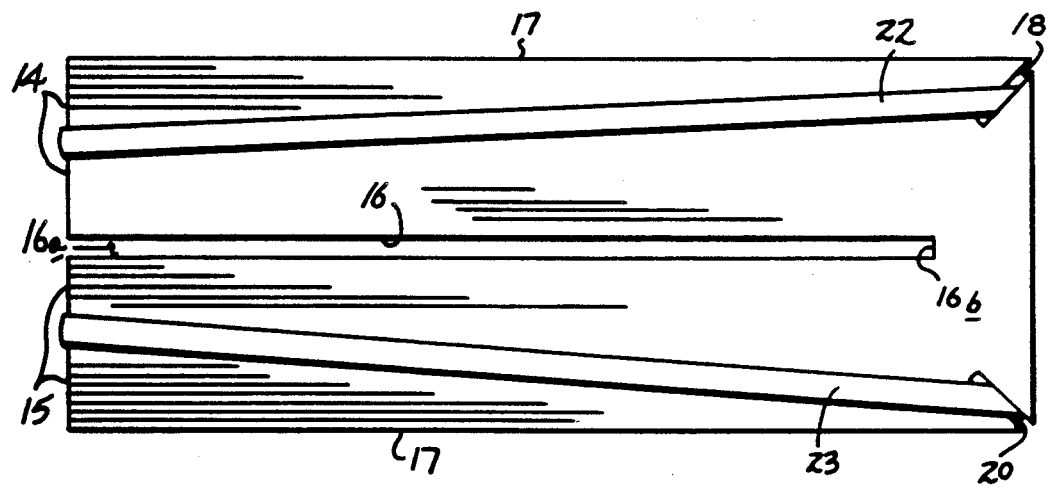
FIG. 2 is a top orthographic view of the instant invention in a first position.
Figure 3:
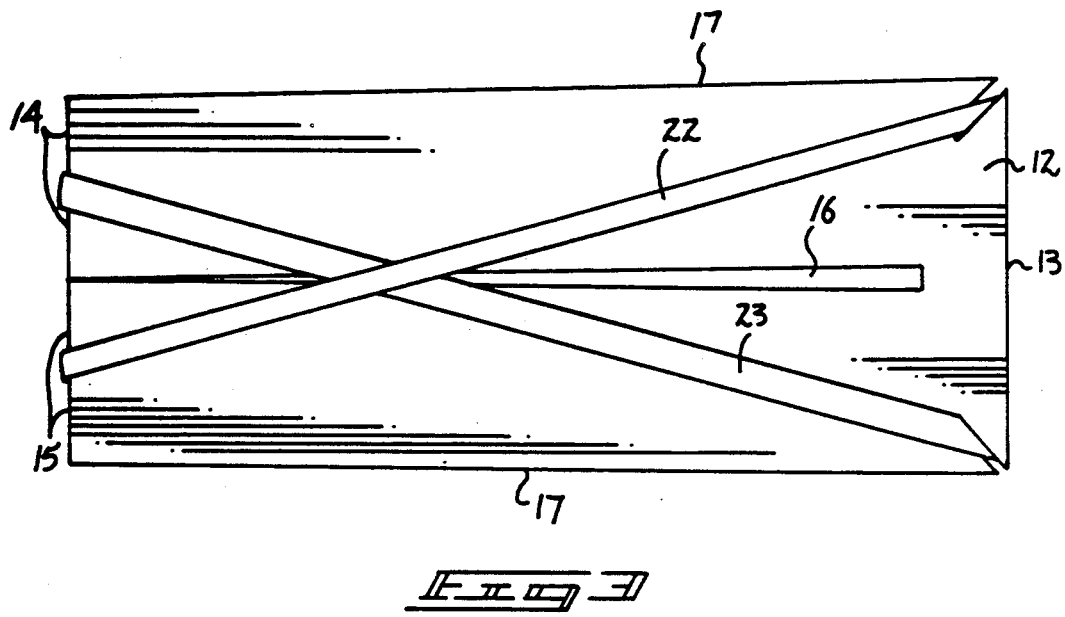
FIG. 3 is a top orthographic view of the instant invention in a second position.
Figure 4:
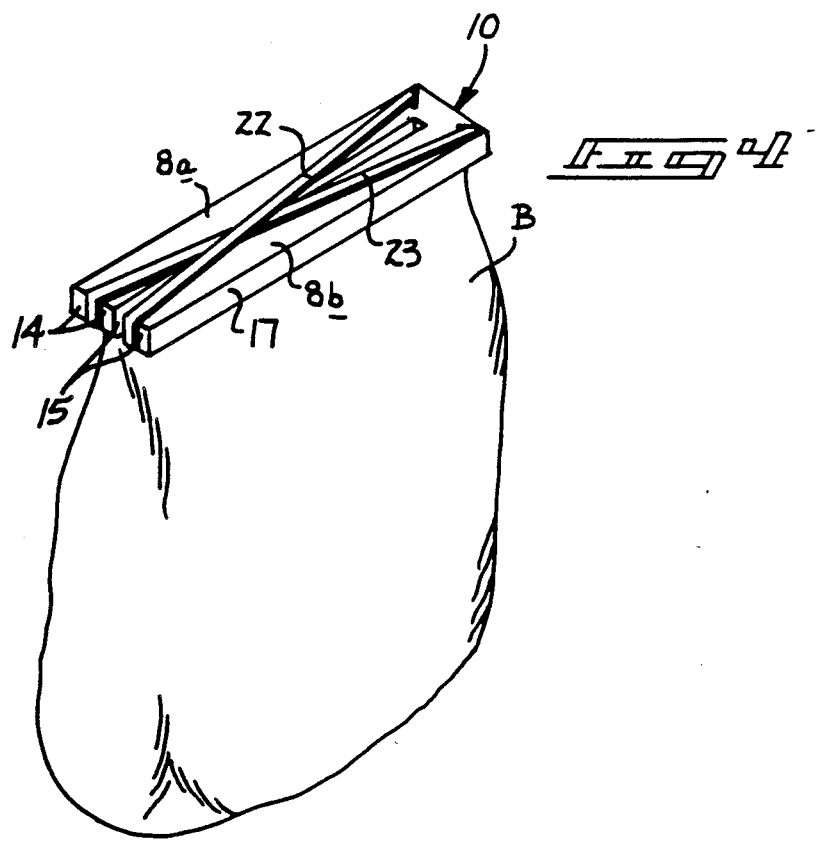
FIG. 4 is an isometric illustration of the instant invention in the second position.

With reference now to the drawings, and in particular to FIGS. 1 to 4 thereof, a new and improved ostomy bag closure device embodying the principles and concepts of the present invention and generally designated by the reference numeral 10 will be described.

More specifically, the ostomy bag closure device 10 essentially comprises a polymeric block 8 formed of memory retentent material of a rectangular parallelepiped configuration. The block includes a top planar wall surface 12 parallel to and overlying a bottom planar wall surface with a rear wall surface 13 parallel to spaced first and second forward wall surfaces 14 and 15 that lie in a common plane. The rear wall surface 13 intersects side walls 17 to define a first slot 18 and a second slot 20. The first and second slots 18 and 20 project interiorly of the block originating at respective corner intersections of the spaced side walls 17 and rear wall 13. The first and second grooves 19 and 21 are defined as arcuate recesses bisecting the first and second planar forward wall surfaces 14 and 15 respectively. The grooves 19 and 21 are directed orthogonally relative to the top and bottom planar surfaces of the block 8. A slot 16 is positioned medially of the grooves defined as first and second grooves 19 and 21 and is parallel to the side wall 17 of the block 8 and includes an entrance end 16a extending interiorly lengthwise of the block parallel to sides 17 and terminating in a closed end 16b spaced a predetermined distance from the rear wall surface 13 orthogonally oriented to rear wall 13. The length of the slot 16 is of an extent to include substantially two-thirds to three-fourths the predetermined length of the block defined along the side walls 17.

A first resilient band 22 and a second resilient band 23 are provided and are of a non-stretched perimeter less than that defined by a distance between the respective grooves 19 and 21 and first and second slots 18 and 20. The first resilient band 22 is secured within the first slot 18 and received within the first groove 19 with the second band 23 secured within the second slot 20 and second groove 21 in a first position. Upon directing a ostomy bag B through the slot 16, and winding an upper end of the bag about the block 8, the first and second resilient bands 22 and 23 are stretched and crossed relative to one another wherein the first band 22 occupies the slot groove 19 and second groove 20, while the second resilient band occupies the slots 18 and 21 to thereby direct the bifurcated first and second fingers 8a and 8b of the block 8 into a pinching relationship relative to the bag B to thereby secure the bag within the slot 16 to effect a closure thereof.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specifications are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ostomy bag closure device in combination with a flexible bag, wherein the closure device comprises an elongate block including an elongate slot directed longitudinally of the block defining spaced first and second confronting surfaces for receiving an upper end of the bag therebetween, and first and second resilient members securable in a first position longitudinally secured to the block, and further positionable in a second crossed position on the block to bias the first and second confronting surfaces towards one another.

2. An ostomy bag closure device as set forth in claim 1 wherein the elongate slot formed within the block means is defined by the first and second confronting surfaces, and the elongate slot is of a predetermined length less than a block length defined by the block.

3. As ostomy bag closure device as set forth in claim 2 wherein the block means is defined by a bifurcated block formed of a polymeric memory retentent material.

4. An ostomy bag closure device as set forth in claim 3 wherein the block includes spaced first and second forward wall surfaces aligned in a single plane, the forward wall surfaces spaced from a rear wall surface, and spaced first and second parallel side wall surfaces respectively extending from the first and second forward wall surfaces to the rear wall surface, and a first arcuate groove bisecting the first forward wall surface on a first side of the slot and a second arcuate groove bisecting the second forward wall surface on a second side of the slot, wherein the arcuate grooves receive the resilient members in respective first and second positions, and first and second slits directed interiorly of the block respective originating from respective intersections of the first and second side wall surfaces and the rear wall surface.

5. An ostomy bag closure device as set forth in claim 4 wherein the slot of a predetermined length is substantially equal to two-thirds to three-quarters of the length of the block, and wherein the slot is positioned medially between opposed elongate sides of the block and positioned medially between the first and second grooves extending rearwardly of the first and second grooves orthogonally oriented to the rear wall surface.

* * * * *